(12) United States Patent
Karmaker et al.

(10) Patent No.: US 7,998,375 B2
(45) Date of Patent: Aug. 16, 2011

(54) METHOD OF MANUFACTURING HIGH STRENGTH DENTAL RESTORATIONS

(75) Inventors: Ajit Karmaker, Wallingford, CT (US);
Mike Karlak, Seymour, CT (US);
Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 623 days.

(21) Appl. No.: 11/946,960

(22) Filed: Nov. 29, 2007

(65) Prior Publication Data
US 2008/0145820 A1    Jun. 19, 2008

Related U.S. Application Data

(63) Continuation-in-part of application No. 10/839,696, filed on May 5, 2004, now abandoned.

(60) Provisional application No. 60/468,935, filed on May 8, 2003.

(51) Int. Cl.
*A61C 13/08* (2006.01)
*B29C 35/10* (2006.01)
*B29C 67/00* (2006.01)
*B29C 70/52* (2006.01)
*B28B 11/16* (2006.01)

(52) U.S. Cl. ......... 264/19; 264/477; 264/495; 264/136; 264/137; 264/145; 264/171.13; 264/171.23; 264/171.24; 264/172.11; 264/236; 156/166; 156/180; 156/433; 433/220; 433/222.1; 433/225; 433/228.1

(58) Field of Classification Search ......... None
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,751,399 A | 8/1973 | Lee et al. | |
| 3,926,906 A | 12/1975 | Lee, II et al. | |
| 4,544,359 A | 10/1985 | Waknine | |
| 4,547,531 A | 10/1985 | Waknine | |
| 5,276,068 A | 1/1994 | Waknine | |
| 5,444,104 A | 8/1995 | Waknine | |
| 5,449,703 A | 9/1995 | Mitra et al. | |
| 5,700,417 A * | 12/1997 | Fernyhough et al. | 264/477 |
| 5,869,178 A * | 2/1999 | Kusy et al. | 428/335 |
| 5,916,509 A * | 6/1999 | Durhman | 264/477 |
| 5,935,508 A * | 8/1999 | Fernyhough et al. | 264/495 |
| 5,969,000 A | 10/1999 | Yang et al. | |
| 6,013,694 A | 1/2000 | Jia et al. | |
| 6,099,783 A | 8/2000 | Scranton et al. | |

(Continued)

OTHER PUBLICATIONS

Trujillo, M. And Stanbury, J.W., "Thermal Effects on Composite Photopolymerization Monitored by Real-time NIR," Mar. 14, 2003, Abstract, University of Colorado Health Sciences Center, Denver, Colorado.

(Continued)

*Primary Examiner* — Jeffrey Wollschlager
(74) *Attorney, Agent, or Firm* — Wood, Herron & Evans, LLP

(57) ABSTRACT

Fiber-reinforced composite posts are produced having high strength and high radiopacity. In a method of manufacturing the fiber-reinforced composite posts, fibers are pulled through filled resin and heat is applied at various steps in the process to provide high strength and optimal radiopacity.

21 Claims, 2 Drawing Sheets

U.S. PATENT DOCUMENTS

| | | | |
|---|---|---|---|
| 6,126,922 | A | 10/2000 | Rozzi et al. |
| 6,186,791 | B1 * | 2/2001 | Karmaker et al. ............ 433/220 |
| 6,236,020 | B1 | 5/2001 | Friedman |
| 6,270,562 | B1 | 8/2001 | Jia |
| 6,320,162 | B1 | 11/2001 | Friedman |
| 6,326,417 | B1 | 12/2001 | Jia |
| 6,386,865 | B1 | 5/2002 | Suh et al. |
| 6,403,676 | B1 | 6/2002 | Jia et al. |
| 6,417,246 | B1 | 7/2002 | Jia et al. |
| 6,439,890 | B1 * | 8/2002 | Karmaker et al. ............ 433/220 |
| 6,455,608 | B1 | 9/2002 | Jia et al. |
| 6,653,365 | B2 | 11/2003 | Jia |
| 6,787,629 | B2 | 9/2004 | Jia et al. |
| 6,827,576 | B2 * | 12/2004 | Karmaker et al. ............ 433/220 |
| 7,241,856 | B2 | 7/2007 | Jin et al. |
| 7,488,175 | B2 * | 2/2009 | Karmaker et al. ............ 433/220 |
| 2002/0014302 | A1 * | 2/2002 | Fanucci et al. ................ 156/179 |
| 2002/0120033 | A1 | 8/2002 | Jia et al. |
| 2002/0156152 | A1 | 10/2002 | Zhang et al. |
| 2002/0198282 | A1 | 12/2002 | Jia |
| 2003/0125444 | A1 | 7/2003 | Jia et al. |
| 2005/0123881 | A1 * | 6/2005 | Karmaker et al. ............ 433/220 |

OTHER PUBLICATIONS

Vaidyanathan et al., "Interactive effects of resin composition and ambient tempreature of light curing on the percentage conversion, molar heat of cure and hardness of dental composite resins," Journal of Materials Science: Materials in Medicine, 3, (1992), p. 19-27.

Pfeifer et al., "Factors Affecting Photopolymerization Stress in Dental Composites", J. Dent. Res., vol. 87 (11), pp. 1043-1047 (2008).

Watts, David, "Reaction kinetics and mechanics in photo-polymerization networks", Dental Materials, vol. 21, pp. 27-35 (2005).

U.S. Patent and Trademark Office, Advisory Action received in related U.S. Appl. No. 10/839,696 dated Feb. 4, 2009, 4 pp.

U.S. Patent and Trademark Office, Non-Final Office Action received in related U.S. Appl. No. 10/839,696 dated Apr. 28, 2009, 23 pp.

U.S. Patent and Trademark Office, Final Office Action received in related U.S. Appl. No. 10/839,696 dated Oct. 19, 2009, 12 pp.

U.S. Patent and Trademark Office, Restriction Requirement received in related U.S. Appl. No. 10/839,696 dated Mar. 18, 2008, 6 pp.

U.S. Patent and Trademark Office, Final Office Action received in related U.S. Appl. No. 10/839,696 dated Oct. 17, 2008, 11 pp.

U.S. Patent and Trademark Office, Non-Final Office Action received in related U.S. Appl. No. 10/839,696 dated Jun. 25, 2008, 15 pp.

* cited by examiner

METHOD OF MANUFACTURING HIGH STRENGTH DENTAL RESTORATIONS

CROSS-REFERENCE TO RELATED APPLICATIONS

This application is a continuation-in-part of U.S. application Ser. No. 10/839,696, filed May 5, 2004, now abandoned which claims priority to U.S. Application No. 60/468,935 filed May 8, 2003, all of which are hereby incorporated by reference.

FIELD OF THE INVENTION

The present invention relates generally to methods of manufacturing dental posts and more specifically to methods of manufacturing light curable fiber-reinforced polymeric composite dental posts.

BACKGROUND OF THE INVENTION

Light curable dental restorative materials are composite compositions of unsaturated functional monomers and fillers that are formulated to be polymerized by photochemical action upon exposure to light. The compositions will typically polymerize upon application of light in the 300-500 nanometer range. These composites have exhibited good mechanical properties after polymerization has been affected. Moreover, polymerizing the composites in inert atmospheres, under compressed air or in a vacuum has further enhanced the mechanical properties.

U.S. Pat. Nos. 6,320,162 and 6,236,020 to Friedman, which are hereby incorporated by reference, are directed to a method and apparatus for preheating single dose units of photocurable materials prior to clinical usage to enhance the properties of the composite. The patents describe the principal advantages of the preheating step as improved monomer conversion, improved material hardness, improved wear resistance, improved color stability, and improved strength. The inventor therein discovered that the reactive monomer in the photocurable material converted to a polymer in a substantially linear relationship over a temperature range from the refrigeration temperature of 20° F. to an elevated temperature of 150° F. Despite the advantages realized by this process, the inventor failed to note that by the time the photocurable material is delivered and shaped into a tooth cavity, the temperature of the material has cooled down to about 98° F. (body temperature). It is not much different than using an unheated photocurable material that will reach the temperature in the patient's mouth, i.e., 98° F., during insertion and before light curing. Moreover, the inventor cannot perform this procedure at temperatures higher than 150° F., since the procedure is being performed in a patient's mouth, and pulpal damage could begin to occur at that point. Therefore, the utilization of elevated temperature for a dental composite is minimal, and the benefit of such is limited.

Fiber-reinforced composite posts in the dental industry have exhibited adequate strength and light translucency, but have been deficient in radio-opacity. In order to increase the radio-opacity, it would be necessary to add more filler to the resin. The addition of more filler tends to increase the viscosity of the filled resin rendering it nearly impossible for penetration of the resin into the fibers.

Accordingly there remains a need to provide high strength fiber-reinforced composite posts having adequate strength and high radio-opacity. It would be beneficial to provide a facile and effective process for manufacturing high-strength and highly radiopaque fiber-reinforced composite posts.

SUMMARY OF THE INVENTION

The above-described drawbacks and disadvantages are alleviated by the method of the present invention for use with photo-initiated polymerizable dental compositions. The method comprises preheating a tooth restoration precursor of a defined shape or anatomy in a temperature range from about 65°-120° C. for a length of time for the temperature to reach a temperature equilibrium. The time preferably ranges from about 1 minute to 30 minutes, more preferably from about 1 to about 15 minutes and most preferably less than about ten minutes. Thereafter, the dental composition is light cured to polymerize the dental restoration precursor. The restoration produced through this process will have at least 10% or higher strength than the dental restorations made by conventional methods.

In an alternate embodiment, fiber-reinforced composite posts are produced having high strength and high radiopacity. In a method of manufacturing the fiber-reinforced composite posts, fibers are polled through filled resin and heat is applied at various steps in the process to provide high strength and optimal radiopacity.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figure 1:
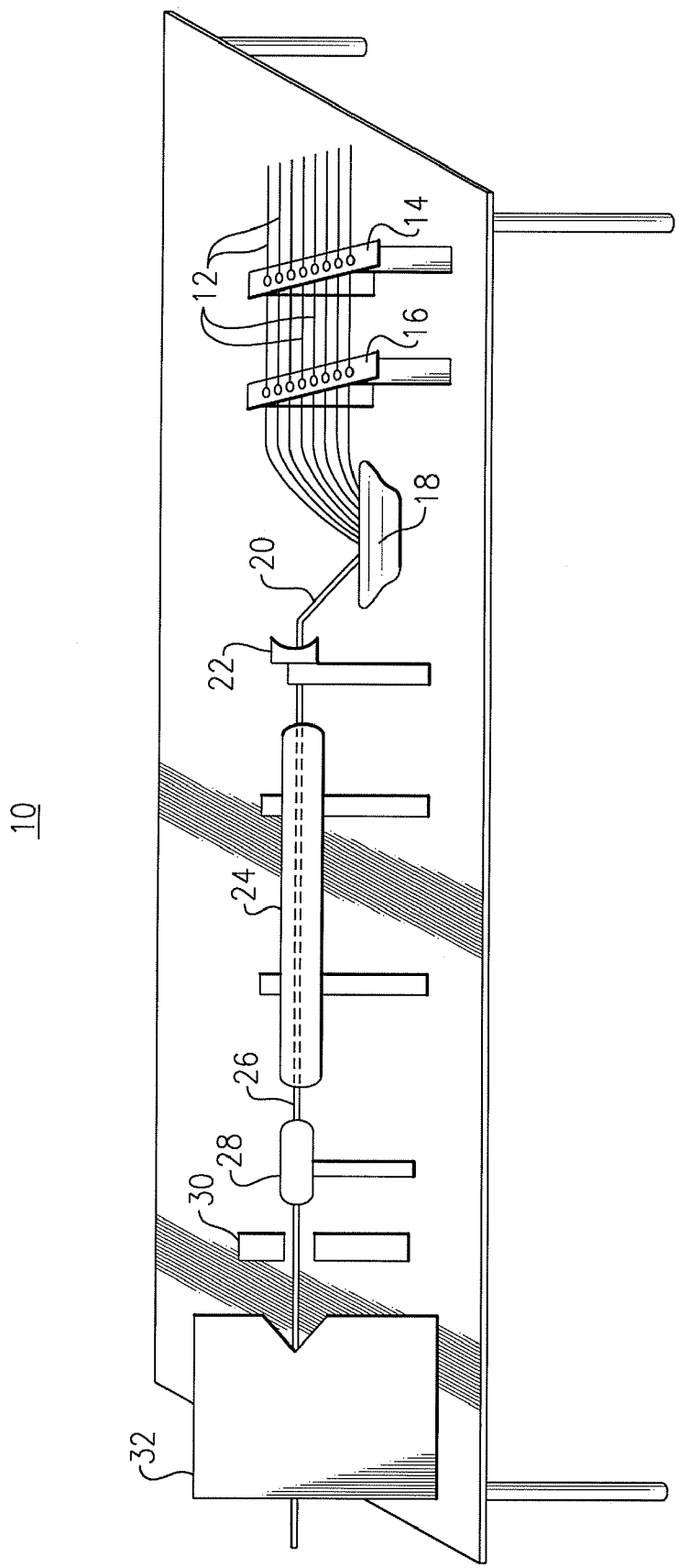
FIG. 1 is a perspective view of the manufacturing system of the present invention.

As will be appreciated, the present invention provides high strength dental composite materials. The process herein is useful in the dental laboratory in the fabrication of dental restorative materials that are subsequently sent to the dentist for placement in the patient's mouth. The dental restorative materials include single and multi-unit dental materials not limited to orthodontic appliances, bridges, space maintainers, tooth replacement appliances, splints, crowns, partial crowns, dentures, posts, teeth, jackets, inlays, onlays, facings, veneers, facets, implants, abutments, cylinders, and connectors.

The process involves forming or molding a composite material comprising a photo-initiated polymerizable reactive monomer into the desired dental restorative shape. The molded or formed shape is then preheated at a temperature in the range from about 65° C. to about 120° C., preferably from about 70° C. to about 110° C. and more preferably from about 75° C. to about 100° C., for a period of time in order for the composite material to reach a temperature equilibrium. It is thought that this preheating step creates higher double bond conversions of the monomer upon light curing polymerization, which gives improved strength to the composite compositions. Without being bound to any theory, the elevated temperature may further aid in softening the viscosity of the composite mass, increasing the resin functional mobility, relaxing any stress from the restoration build-up process, reorganizing the resin molecular orientation, and freeing or minimizing voids within the mass. All of these effects will help to improve the properties of the cured mass. Following this preheating step, the preheated shape is immediately light cured to promote full polymerization of the monomer to harden the dental restorative shape.

As described above, the process herein is for use with light-curable dental restorative composites wherein a photoinitiator is present to initiate curing by light radiation. The composition comprises a polymerizable component, i.e., at least one polymerizable monomer or prepolymer selected from those known in the art of dental materials, including but not being limited to, resins having (1) free radically active functional groups, (2) cationically active functional groups, and (3) both free radically and ionically active groups.

Examples of free radical polymerizable resins include, but are not limited to those resins with ethylenically unsaturated functional groups, such as (meth)acrylates; vinyl monomers, such as styrene; vinyl esters; and a variety of unsaturated cyclic monomers, such as spiro ortho carbonates or esters, vinyl cyclic ethers and cyclic acetals.

Examples of resins having ionically active functional groups include, but are not limited to, vinyl ethers and a variety of cyclic monomers that are susceptible to cationic or anionic ring-opening, such as epoxies, siloranes, lactide, ε-caprolactones and ε-caprolactam.

Examples of resins containing both free radical and ionically curable functional groups include, but are not limited to the resin oligomers having both an epoxy functionality and a (meth)acrylate functionality as set forth in commonly owned U.S. Pat. No. 7,241,856, which is hereby incorporated by reference.

Preferred polymerizable monomers are ethylenically unsaturated and include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat No. 5,276,068 to Waknine, all of which are herein incorporated by reference in their entirety. Methacrylate-based monomers are particularly preferred, including the condensation product of bisphenol A and glycidyl methacrylate, 2,2'-bis[4-(3-methacryloxy-2-hydroxy propoxy)-phenyl]-propane ("BIS-GMA"), dipentaerythritol pentaacrylate (DPEPA), pentaerythritol dimethacrylate (PEDM), the condensation product of ethoxylated bisphenol A and glycidyl methacrylate ("EBPA-DMA"), urethane dimethacrylate (UDMA), ethoxylated bisphenol A di(meth) acrylates including ethoxylated bisphenol A dimethacrylate (EBPDMA) as disclosed in U.S. Pat. No. 6,013,694 to Jia, et al., and the condensation product of 2 parts hydroxymethylmethacrylate and 1 part triethylene glycol bis(chloroformate) ("PCDMA"). Polyurethane-based dimethacrylates ("PUDMA") and polycarbonate modified-BisGMA (PCBis-GMA) and other monomers set forth in commonly owned U.S. Pat. No. 6,787,629, which is hereby incorporated by reference, are also within the scope of the present invention.

The polymerizable component may further comprise additional polymerizable diluent monomers. Such monomers are generally used to adjust the viscosity of the polymerizable composition. Suitable methacrylate-based diluent monomers include, without limitation, hydroxyalkyl methacrylates, such as 2-hydroxyethyl methacrylate, 1,6-hexanediol dimethacrylate (HDDMA), and 2-hydroxypropyl methacrylate; glyceryl dimethacrylate; and ethylene glycol methacrylates, including ethylene glycol methacrylate, diethyleneglycol methacrylate, triethyleneglycol methacrylate and tetraethyleneglycol methacrylate. Triethyleneglycol dimethacrylate ("TEGDMA") is particularly preferred.

The dental restorative composition furthermore includes a polymerization photoinitiator system for light curing the polymeric material. The light cure system is selected from known light-activated polymerization initiators, including but not being limited to benzil, benzoin, benzoin methyl ether, DL-camphorquinone (CQ) and benzil diketones. Either UV-activated cure or visible light-activated cure (approx. 230 to 750 nm) is acceptable. The amount of photoinitiator is selected according to the curing rate desired. A minimally catalytically effective amount is generally about 0.01% by weight of the polymeric components. Faster rates of cure are achieved with amounts of catalyst in the range from greater than about 0.01% to about 5% by weight of the polymeric component. Visible light curing systems furthermore preferably comprise polymerization accelerators, which include various organic tertiary amines well known in the art. In visible light curable compositions, the tertiary amines can be acrylate derivatives such as dimethylaminoethyl methacrylate and, particularly, diethylaminoethyl methacrylate ("DEAME") and aromatic tertiary amines such as ethyl dimethylamino benzoate (EDMAB) in amounts in the range from about 0.05 to about 2 weight percent and preferably from about 0.1 to about 0.5 weight percent.

The dental restorative compositions may also comprise other additives and solvents known in the art, for example, ultra-violet light absorbers, anti-oxidants such as BHT, stabilizers, fillers, pigments, opacifiers, handling agents, and others. It is preferred to employ an ultraviolet absorber in amounts ranging from about 0.05 to about 5.0 weight percent. Such UV absorbers are particularly desirable in these visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

Fillers, such as particulate and fibers, colloidal silica, barium glasses, fibrous fillers, quartz, ceramic fillers and the like may also be incorporated into the compositions. Suitable fillers include fillers conventionally used in the dental industry capable of being covalently bonded to the resin matrix itself or to a coupling agent which is covalently bonded to both. Silane coupling agents are known, for example methacryloxypropyl trimethoxy silane. Such fillers are described in U.S. Pat. Nos. 4,544,359 and 4,547,531, the pertinent portions of which are hereby incorporated by reference. Examples of suitable filling materials include but are not limited to amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders such as polymethyl methacrylate, polystyrene, and polyvinyl chloride, titania, bound, nanostructured silica fillers as set forth in commonly owned U.S. Pat, No. 6,417,246, which is hereby incorporated by reference, densified, embrittled glass fibers or particles as set forth in commonly owned U.S. Pat. Nos. 6,013,694 and 6,403,676, which are hereby incorporated by reference, fibrous material and one or more forms of surface-modifying particles bonded thereto as set forth in commonly owned U.S. Pat. No. 6,270,562, which is hereby incorporated by reference, and polyhedral oligomeric silsesquioxane fillers as set forth in U.S. Pat. No. 6,653,365, which is hereby incorporated by reference, and combinations of all the fillers mentioned. Particularly suitable fillers for dental filling-type materials prepared are those having a particle size in the range from about 0.1 to about 5.0 microns, together with a silicate colloid having particle sizes in the range from about 0.001 to about 0.07 microns.

In accordance herein, the dental restoration is molded into the desired form using a polymeric composite material, as described above. The molded shape is then preheated at a temperature in the range from about 65° C. to about 120° C. for a period of time such that the composite reaches temperature equilibrium in the desired range. The molded shape may be maintained at this temperature for about 1 to about 30 minutes, preferably for about 1 to about 15 minutes, and most preferably less than about 10 minutes, before it is subjected to light curing. Thereafter the material is subjected to light curing to fully harden the dental restoration. It is preferable that the high temperature (i.e., between about 65° and 120° C.) is maintained during the light curing step to obtain optimal benefits from the process. After curing, the restoration may be further subjected to surface grinding, trimming, finishing, polishing and cleaning before being delivered into the patient's mouth. The restoration is now ready for placement in the patient's mouth with a conventional cementation media as preferred by a dentist.

In accordance with another aspect of the invention herein, a curing apparatus is provided wherein a polymeric dental material may be heated at the preheating temperature range of from about 65° C. to about 120° C. The polymeric dental material may be further light cured in the same apparatus, optionally allowing for the temperature to be maintained while light curing is performed. The apparatus may include two separate compartments, one for preheating and one for light curing, or it may include a single compartment wherein preheating and light curing are performed. The preheating step is performed prior to light curing and may be maintained during the light curing operation.

The following examples do not limit, but further illustrate the invention.

EXAMPLE 1

A light curable only Sculpture Plus® restorative composite material, Shade A2, lot #75806 (available from Pentron Laboratory Technologies, LLC, Wallingford, Conn.) was used for this strength test. The test sample size was 2×2×25 mm as defined by ISO Specification No. 4049 for dental resin based restorative materials. The composite material was packed into a metal mold and covered with glass slides on both sides. The whole ensemble was then placed into an oven with a preset temperature as indicated in the Table 1 below for 15minutes to reach temperature equilibrium. Immediately after heating at the predetermined temperature, the whole ensemble was immediately placed (within 5 seconds) into the Cure-Lite Plus™ curing light unit for 4 minutes of photo-curing. Six samples for each test group were prepared. The samples were trimmed to remove any excess and aged for 24 hours in water at 37° C. before performing the three-point bend flexural strength test with an ATS machine. The results are as listed in the Table 1 below.

TABLE 1

| Sculpture Plus composite preheated for 15 min. at the following temperatures | Three-Point Bend Test (flexural strength) (psi)(SD) | Percent Strength Increase Resulting From Heating Above 65° C. In Comparison to No Heating |
|---|---|---|
| No heating (about 20° C.) | 19476(2019) | |
| 40° C. | 20678(1386) | |
| 70° C. | 22656(1222) | 16.32% |
| 120° C. | 21650(2320) | 11.16% |

EXAMPLE 2

Commercial light curable dental restorative composites designed for direct dentist use or indirect lab technician use were tested for resistance to crush. Alert® composite (available from Pentron Clinical Technologies, LLC, Wallingford, Conn.) is a tooth filling material used by a dentist at chairside. The material was tested here to illustrate the preheating effects to a dental resin composite material. Sculpture® and Sculpture® Plus composites are two generations of laboratory restorative composites that have different resin matrix compositions as disclosed in U.S. Pat. Nos. 5,276,068, 5,969,000, 4,544,359, and 5,444,104, and U.S. application Ser. No. 10/287,428, all of which are commonly assigned and which are hereby incorporated by reference. FiberKor® material is a resin pre-impregnated unidirectional glass fiber containing strip material used to reinforce a dental restoration made from a resin composite material such as Sculpture® composite or Sculpture® Plus composite. All these materials are available from Pentron Laboratory Technologies, LLC.

To make a composite dental crown, a single sized tooth die formed from a #3 core form (available from Pentron Laboratory Technologies, LLC, under the product name of Build-It® Core Forms—Core Build-It® Caps) was duplicated with a dental impression material using the conventional method of impression-taking and stone-pouring with a dental gypsum/stone material. Dental crowns/caps were fabricated on the tooth dies with a larger-sized transparent crown form (size #6) as a cap to sit onto the tooth die with sufficient materials filled in. The assemblies were then subjected to various pre-heating tempera lure settings for 5 minutes in a digitized Boekel lab oven (Model 133000) (Boekel Industrial, Inc.) immediately before placing into the Cure-Lite Plus curing unit for 4 minutes. Losing the crown forms to fabricate the testing crowns will ensure the uniform sizes/forms of the crowns formed and make the testing results relevant. After the composite crowns/caps were polymerized, the flexible transparent core form caps were lifted and removed from the composite crowns. The hardened composite crowns/caps were subsequently removed from the stone dies. Further trimming on the edges of the crowns to remove any excess material was performed where necessary before putting the crowns into water and aging for 24 hour at 37° C. Each set of testing crowns had six samples. The crowns/caps were placed onto a flat platform and crushed under the compression mode with a crosshead speed of 0.2 in/min. with an ATS Model 1105 testing machine (Applied Testing Systems, Inc.). The maximum load at which the crown was fractured and detected by the machine was recorded in the force unit of pounds (lb). The average and standard deviations were calculated by the machine after the testing was finished.

The testing results from the experiments show that preheating a light curable dental composite at a temperature in the range from about 65° to about 120° C., followed by immediate light polymerization can increase the strength of the cured material or resistance to crush by at least 10 percent. The results are shown in Table 2 below.

TABLE 2

| Test Materials | Resistance to Crush For Polymerization at Room Temp. (lbs) | Resistance to Crush For Polymerization at 40° C. (lbs) | Resistance to Crush For Polymerization at 70° C. (lbs) | Resistance to Crush For Polymerization at 90° C. (lbs) |
|---|---|---|---|---|
| Alert ® composite | 292.7 (49.2) | — | 451.2 (90.0) | — |
| Sculpture ® composite | 299.1 (89.6) | — | — | 358.4 (100.9) |
| Sculpture ® Plus composite | 267.9 (84.5) | 344.2 (77.1) | 445.8 (162.4) | — |
| Sculpture ® Plus composite with a layer of FiberKor ® fiber embedded therein | 442.9 (122.4) | 475.8 (123.6) | 531.0 (194.3) | 526.1 (167.8) |

In accordance with an alternate embodiment herein, fiber-reinforced composite posts are manufactured using a pultrusion method whereby fibers are pulled through a system to produce a fiber-reinforced composite post. Reference is made to FIG. 1 which shows a system 10. Fibers 12 are typically provided on spools in single strands or in bundles of fibers.

Fibers 12 are pulled through separators 14 and 16 to resin bath 18 whereby the fibers are immersed in a filled resin and impregnated with the resin to produce a fiber-reinforced composite 20. The filled resin can be heated in the temperature range from about 50 to about 100° C. and more preferably in the range from about 60 to about 90° C.

The fiber-reinforced composite 20 is pulled through a funnel-shaped device 22 to squeeze excess filled resin from the composite 20. Composite 20 is then pulled through die 24 which heats composite 20 and forms composite 20 into a rod-shaped composite 26. The die may be as long as necessary to maintain the heat of the impregnated fibers. Preferably it is about 15 to about 20 inches in length. The heating temperature is in the range from about to 65 to about 125° C., more preferably in the range from about 70 to about 110° C. and most preferably in the range from about 75 to about 100° C. The heating time is in the range of about 10 seconds to about 10 minutes and preferably in the range of about 30 seconds to about 2 minutes. Excess filled resin may be squeezed at the entry and exit of composite 20 into and out of die 24.

Rod-shaped composite 26 is further heated in a smaller, final die 28 at the same or similar temperature and time ranges used in die 28. The size of this smaller die can be in the range from about 1 to about 5 inches in length. The diameter of the smaller die is slightly smaller than the long die and it controls the final diameter of the cured rod. Rod-shaped composite 26 is spot cured in curing device 30 and pulled through curing box 32 whereby it is finally cured into a fiber-reinforced rod. It is then cut at intervals to produce dental posts. Further finishing of the posts such as grinding into desired shapes and sizes and coating with coupling or similar agents may be conducted.

Figure 2:
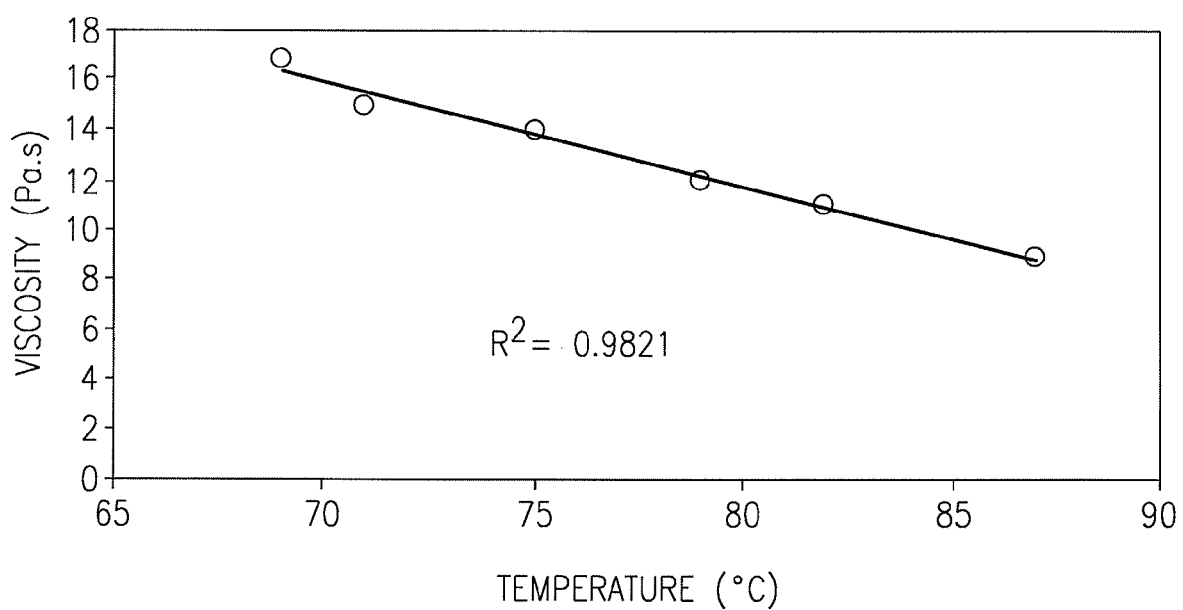
FIG. 2 is a graph showing the effect of temperature on viscosity.

In order to increase the modulus of rupture, the amount of filler is increased. Since high amounts of filler can make it difficult to form the composite into desired shapes, the inventors have found that by heating the filled resin and the fiber, the formability is maintained, even with higher filler content. FIG. 2 shows the effects of heating a filled resin having 70% filler by weight and 30% resin by weight. The filler used herein was barium oxide-containing glass filler and the resin used herein was a mixture of Bis-GMA, UDMA and HDDMA. As shown in FIG. 2, the higher the heating temperature, the lower the viscosity. The correlation coefficient ($R^2$) is 0.9821 which represents a linear relationship between viscosity and temperature. As the resin is heated, the viscosity decreases, allowing for easy forming of the composite having a high amount of filler.

Fibers 12 used in the process can include any fiber known in the art, for example, polyethylene fiber, nylon fiber, polymer fiber, glass fiber (S2, E, AR, ECR, A, C, D, R), graphite fiber, quartz fiber, metal fiber, ceramic fiber, boron fiber, aluminum fiber, or combinations thereof. Fiber is commercially available as yarn or roving that is a bundle of individual filaments on a spool. It is preferable that S2 fiber be used to provide a clear or translucent post. Examples of commercially available fibers include S2 glass fiber from Advanced Glassfiber Yarns, LLC (Aiken, S.C.).

The resin used in the process is a polymerizable component, i.e., at least one polymerizable monomer or prepolymer selected from those known in the art of dental materials, including but not being limited to, resins having (1) free radically active functional groups, (2) cationically active functional groups, and (3) both free radically and ionically active groups. Examples of resins (1), (2) and (3) and preferred polymers are listed above.

The polymerizable component may further comprise additional polymerizable diluent monomers. Such monomers are generally used to adjust the viscosity of the polymerizable composition. Suitable methacrylate-based diluent monomers include, without limitation, hydroxyalkyl methacrylates, such as 2-hydroxyethyl methacrylate, 1,6-hexanediol dimethacrylate (HDDMA), and 2-hydroxypropyl methacrylate; glyceryl dimethacrylate; and ethylene glycol methacrylates, including ethylene glycol methacrylate, diethyleneglycol methacrylate, triethyleneglycol methacrylate and tetraethyleneglycol methacrylate. Triethyleneglycol dimethacrylate ("TEGDMA") is particularly preferred.

The resin component furthermore includes a polymerization photoinitiator system for light curing the polymeric material. The light cure system is selected from known light-activated polymerization initiators, including but not being limited to benzil, benzoin, benzoin methyl ether, DL-camphorquinone (CQ) and benzil diketones. Suitable commercially available phosphine oxide photoinitiators include, for example, the LUCIRIN® series from BASF Corp. such as LUCIRIN® TPO (L-TPO) and LUCIRIN® 8809. Other phosphine oxide photoinitiators may be selected form the DAROCUR® or IRGACURE® series from Ciba-Geigy Corp. Examples include DAROCUR® TPO, DAROCUR® 4265, IRGACURE® 1800 and the like. Either UV-activated cure or visible light-activated cure (approx. 230 to 750 nm) is acceptable. The amount of photoinitiator is selected according to the curing rate desired. A minimally catalytically effective amount is generally about 0.01% by weight of the polymeric components. Faster rates of cure are achieved with amounts of catalyst in the range from greater than about 0.01% to about 5% by weight of the polymeric component. Visible light curing systems furthermore preferably comprise polymerization accelerators, which include various organic tertiary amines well known in the art. In visible light curable compositions, the tertiary amines can be acrylate derivatives such as dimethylaminoethyl methacrylate and, particularly, diethylaminoethyl methacrylate ("DEAME") and aromatic tertiary amines such as ethyl dimethylamino benzoate (EDMAB) in amounts in the range from about 0.05 to about 2 weight percent and preferably from about 0.1 to about 0.5 weight percent.

The resin compositions may also comprise other additives and solvents known in the art, for example, ultra-violet light absorbers, anti-oxidants such as BHT, stabilizers, fillers, pigments, opacifiers, handling agents, and others. It is preferred to employ an ultraviolet absorber in amounts ranging from about 0.05 to about 5.0 weight percent. Such UV absorbers are particularly desirable in these visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TUNIVIN® P by Ciba-Geigy Corporation, Ardsley, N.Y.

The filler in the filled resin can be one or more of the inorganic fillers suitable for use in dental composite materials, including particulate, fibrous and colloidal fillers. Suitable fillers include fillers conventionally used in the dental industry capable of being covalently bonded to the resin matrix itself or to a coupling agent which is covalently bonded to both. Silane coupling agents are known, for example methacryloxypropyl trimethoxy silane. Such fillers are described in U.S. Pat. Nos. 4,544,359 and 4,547,531, the pertinent portions of which are hereby incorporated by reference. Specific examples of suitable filling materials include but are not limited to, silica including fumed silica, quartz, strontium silicate, strontium borosilicate, lithium silicate, lithium alumina silicate, amorphous silica, ammoniated or deammoniated calcium phosphate, tricalcium phosphate, alumina, zirconia, tin oxide, titania, barium borosilicate glass filler, silane treated barium borosilicate glass filler, glass ionomer filler (e.g. Ca—Al—F—Ba-Silicate) amorphous silica, spherical silica, colloidal silica, barium glasses, quartz, ceramic fillers, silicate glass, hydroxyapatite, calcium carbonate, fluoroaluminosilicate, barium sulfate, barium silicate, strontium silicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders such as, polymethyl methacrylate, polystyrene, and polyvinyl chloride, titania, bound, nanostructured, silica fillers as set forth in commonly owned U.S. Pat. No. 6,417,246, which is hereby incorporated by reference, densified, embrittled glass fibers or particles as set forth in commonly owned U.S. Pat. Nos. 6,013,694 and 6,403,676, which are hereby incorporated by reference, fibrous material and one or more forms of surface-modifying particles bonded thereto as set forth in commonly owned U.S. Pat. No. 6,270,562, which is hereby incorporated by reference, and polyhedral oligomeric silsesquioxane fillers as set forth in U.S. Pat. No. 6,653,365, which is hereby incorporated by reference, and combinations of all the fillers mentioned.

Organic-inorganic fillers of POSS® (Hybrid Plastics) can be incorporated into the composites as disclosed in U.S. Patent Application Publication 2002/0198282A1. Other organic-inorganic fillers such as zirconium methacrylate and zirconium dimethacrylate available under the codes of CXZR050 and CXZR051 (Gelest, Inc.) can also be used. Suitable high refractive index filler materials such as high refractive index silica glass fillers; calcium silicate based fillers such as apatites, hydroxyapatites or modified hydroxyapatite compositions may also be used. Alternatively, inert, non-toxic radiopaque materials such as bismuth oxide ($Bi_2O_3$), bismuth oxychloride (BiOCl), zirconium oxide, barium sulfate, ytterbium fluoride, and bismuth subcarbonate in micro- or nanoscaled sizes may be used. In addition, fibrous fillers such as those disclosed in U.S. Pat. Nos. 6,013,694, 6,403,676 and 6,270,562 to Jia and Jia et al. may also be used.

Suitable fillers have particle sizes of about 0.01 to about 5.0 micrometers, and may further comprise bound or unbound silicate colloids of about 0.001 to about 0.2 micrometers. These additional fillers may also be treated with a silane-coupling agent to increase adhesion with the polymerizable (meth)acrylate. Commercially available silane treated fumed silica based on AEROSIL® A200 can be obtained from Degussa Corp under the names of AEROSIL® R711 and R7200.

In order to create highly radiopaque composite material, it is preferable that the filler is a radiopaque filler listed above. Specifically, the filler is present in the range of from about 40 to about 80 percent, and more specifically in the range of from about 50 to about 70 percent. The resin is present in the range from about 20 to about 50 percent, and more specifically in the range from about 30 to about 40 percent. The proportions of the components in the fiber-reinforced composite post are specifically, resin in an amount from about 15 to about 30 percent by weight, filler in an amount from about 15 to about 60 percent by weight, and fiber in an amount from about 20 to about 60 percent by weight. More specifically, resin is present in an amount from about 19 to about 25 percent by weight, filler is present in an amount from about 25 to about 50 percent by weight, and fiber is present in an amount from about 25 to about 50 percent by weight.

The following non-limiting examples illustrate the invention.

EXAMPLE 3

S2 glass fibers were pulled through a filled resin bath containing a resin mixture of Bis-GMA, UDMA and HDDMA and barium oxide filler in the percentages set forth below whereby the fibers were impregnated with the resin. The resin bath was heated and maintained at 60 to 70° C. throughout the process. Excess resin was squeezed out of the impregnated fibers and the fibers continued to be pulled through a heated die for forming into a rod, which die was heated at 75 to 85° C. Excess resin was again squeezed from the impregnated fibers after exiting the heated die. The impregnated fibers were pulled through a second, smaller die, for forming into a rod, which die was heated at 70° C. After exiting the smaller die, the impregnated fibers were pulled through a small curing device that spot cured the rod-shaped impregnated fibers. The rod was then pulled through a curing box for complete curing. The rod was cut into 10 mm sections to provide posts.

EXAMPLE 4

S2 glass fibers were pulled through a filled resin bath containing a resin mixture of Bis-GMA, EBPDMA and HDDMA and two fillers, barium oxide filler (Filler A) and ytterbium fluoride filler (Filler B) in the percentages set forth below in Table 3 whereby the fibers were impregnated with the resin. The resin bath was heated and maintained at 60 to 70° C. throughout the process. Excess resin was squeezed out of the impregnated fibers and the fibers continued to be pulled through a heated die for forming into a rod, which die was heated at 75 to 85° C. Excess resin was again squeezed from the impregnated fibers after exiting the heated die. The impregnated fibers were pulled through a second, smaller die, for forming into a rod, which die was heated at 70° C. After exiting the smaller die, the impregnated fibers were pulled through a small curing device that spot cured the rod-shaped impregnated fibers. The rod was then pulled through a curing box for complete curing. The rod was cut into 10 mm sections to provide posts.

The posts were tested for mechanical properties and for radio-opacity. Table 3 below sets forth the properties of Examples 3 and 4 in comparison to a control which was not made by pultrusion with no heating involved.

TABLE 3

| Post rod-diameter is 1.78 mm and test span is 10 mm | Component (wt %) | MOR | Modulus | Radio-opacity (equivalent 1 mm Al) |
|---|---|---|---|---|
| Control* | Fiber$^1$ = 58<br>Filler$^2$ = 21<br>Resin$^3$ = 21 | 971 ± 106 | 21 ± 1 | .8 |
| Example 3 | Fiber$^1$ = 38<br>Filler$^2$ = 43<br>Resin$^3$ = 19 | 1260 ± 129 | 20 ± 1 | 1.2 |
| Example 4 | Fiber$^1$ = 38<br>Filler A = 37<br>Filler B = 6<br>Resin$^4$ = 19 | 1156 ± 110 | 20 ± 1 | 1.8 |

*FibreKleer ® Posts available from Pentron Clinical Technologies, LLC
$^1$S2 glass fiber
$^2$barium borosilicate glass filler
$^3$mixture of BISGMA, UDMA AND HDDMA
$^4$mixture of BISGMA, EBPDMA AND HDDMA As shown in Table 3, the posts made in accordance with the invention exhibit a higher modulus of rupture and a much higher radio-opacity. Radio-opacity increased by 50-125% and modulus of rupture increased by 20-30% while the modulus of elasticity was maintained at the same level. Accordingly, the posts made in accordance with the claimed invention show optimal strength and radio-opacity properties.

The terms "a" and "an" so not denote a limitation of quantity, but rather denote the presence of at least one of the referenced items. The endpoints of all ranges directed to the same component or property are inclusive and independently combinable. All references are incorporated by reference herein.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of manufacturing a fiber-reinforced composite dental post comprising:
   pulling fibers through a heated reservoir having a filled resin therein, wherein the filled resin comprises a resin component including a photo-initiated polymerizable reactive monomer and a radiopaque filler component in an amount of about 40 to about 80 percent by weight, wherein the filled resin is heated to a temperature in a range from about 50° C. to about 100° C., and wherein the fibers are immersed in and impregnated with the filled resin to produce a fiber-reinforced composite comprising the resin component in an amount from about 15 to about 30 percent by weight, the filler component in an amount from about 15 to about 60 percent by weight, and the fibers in an amount from about 20 to about 60 percent by weight;
   pulling the fiber-reinforced composite through a first heated rod-shaped die having a first diameter and length, whereby the fiber-reinforced composite is shaped into a rod and heated a first time at a temperature in a range from about 65° C. to about 125° C.;
   continuing to pull the fiber-reinforced composite through a second heated rod-shaped die having a second diameter smaller than the first diameter and/or a second length smaller than the first length, wherein the fiber-reinforced composite is heated a second time at a temperature in a range from about 65° C. to about 125° C.; and
   after the fiber-reinforced composite exits the second heated rod-shaped die, light curing the fiber-reinforced composite as it passes through a light curing device to effect polymerization of the photo-initiated polymerizable reactive monomer and to fully harden the fiber-reinforced composite into a cured rod.

2. The method of claim 1 further comprising cutting the rod into smaller sections to provide a dental post.

3. The method of claim 1 wherein light curing the fiber-reinforced composite comprises first spot light curing the fiber-reinforced composite and secondly fully light curing the fiber-reinforced composite in a light box.

4. The method of claim 1 wherein the resin component comprises (1) a resin having free radically active functional groups, (2) a resin having cationically active functional groups, or (3) a resin having a mixture of both free radically and ionically active functional groups.

5. The method of claim 4 wherein the resin having free radically active functional groups comprises ethylenically unsaturated functional groups.

6. The method of claim 5 wherein the ethylenically unsaturated functional groups comprise (meth)acrylates, vinyl monomers, unsaturated cyclic monomers, or a mixture thereof.

7. The method of claim 5 wherein the resin having a mixture of both free radically and ionically active functional groups comprises an oligomer having both an epoxy functionality and a (meth)acrylate functionality.

8. The method of claim 1 wherein the photo-initiated polymerizable reactive monomer comprises an acrylic monomer, a methacrylic monomer or a mixture thereof.

9. The method of claim 1 wherein the photo-initiated polymerizable reactive monomer comprises at least one component selected from the group consisting of the condensation product of bisphenol A and glycidyl methacrylate, 2,2'-bis[4-(3-methacryloxy-2-hydroxy propoxy)-phenyl]-propane ("BIS-GMA"), dipentaerythritol pentaacrylate (DPEPA), pentaerythritol dimethacrylate (PEDM), the condensation product of ethoxylated bisphenol A and glycidyl methacrylate ("EBPA-DMA"), the condensation product of 2 parts hydroxymethylmethacrylate and 1 part triethylene glycol bis (chloroformate) ("PCDMA"), urethane dimethacrylate ("UDMA"), polyurethane-based dimethacrylates ("PUDMA"), and polycarbonate modified-BisGMA (PCBis-GMA).

10. The method of claim 1 wherein the resin component further includes one or more polymerizable diluent monomers selected from the group consisting of hydroxyalkyl methacrylates, glyceryl dimethacrylate, and ethyleneglycol methacrylates.

11. The method of claim 10 wherein the hydroxyalkyl methacrylates are selected from 2-hydroxyethyl methacrylate, 1,6-hexanediol dimethacrylate, or 2-hydroxypropyl methacrylate.

12. The method of claim 10 wherein the ethyleneglycol methacrylates are selected from ethyleneglycol methacrylate, diethyleneglycol methacrylate, triethyleneglycol methacrylate, tetraethyleneglycol methacrylate or triethyleneglycol dimethacrylate ("TEGDMA").

13. The method of 1 wherein the filler component comprises particulate fillers, fibers and mixtures thereof.

14. The method of claim 1 wherein the filler component comprises barium glasses, barium sulfate, barium silicate, barium borosilicate, barium boroaluminosilicate, strontium borosilicate, strontium boroaluminosilicate, bismuth oxide, bismuth oxychloride, zirconium oxide, ytterbium fluoride, bismuth subcarbonate, and combinations thereof.

15. The method of claim 1 wherein the fiber comprises S-glass, AR-glass, ECR-glass, A-glass, C-glass, D-glass, E-glass, R-glass, graphite, quartz, metal, ceramic, boron, aluminum, polyethylene, nylon, polymer or mixtures thereof.

16. The method of claim 1 wherein the filled resin further comprises colorants, stabilizers, whitening agents, antioxidants, photosensitizers, medicaments or a mixture thereof.

17. The method of claim 1 further comprising squeezing excess filled resin from the fiber-reinforced composite prior to heating the fiber-reinforced composite the first time.

18. The method of claim 1 further comprising squeezing excess filled resin from the fiber-reinforced composite after heating the fiber-reinforced composite the first time.

19. The method of claim 1 wherein the fiber-reinforced composite is heated for the first time from about 10 seconds to about 10 minutes inside the first heated rod-shaped die.

20. The method of claim 1, wherein the second diameter is smaller than the first diameter.

21. The method of claim 1, wherein the fiber-reinforced composite comprises the resin component in an amount from about 19 to about 25 percent by weight, the filler component in an amount from about 25 to about 50 percent by weight, and the fibers in an amount from about 25 to about 50 percent by weight.

* * * * *